United States Patent [19]
Leeb

[11] Patent Number: 5,375,322
[45] Date of Patent: Dec. 27, 1994

[54] METHOD OF MANUFACTURING CIRCUIT BOARD HAVING LATERAL CONDUCTIVE PATTERN

[75] Inventor: Karl-Erik Leeb, Djurhamn, Sweden

[73] Assignee: Telefonaktiebolaget L M Ericsson, Stockholm, Sweden

[21] Appl. No.: 155,818

[22] Filed: Nov. 23, 1993

Related U.S. Application Data

[62] Division of Ser. No. 897,829, Jun. 12, 1992, Pat. No. 5,298,684.

[30] Foreign Application Priority Data

Jun. 14, 1991 [SE] Sweden ............................ 9101837

[51] Int. Cl.$^5$ ........................................... H05K 3/02
[52] U.S. Cl. .................................... 29/846; 29/830; 257/703; 257/737
[58] Field of Search ............... 29/846, 830; 257/703, 257/737

[56] References Cited

U.S. PATENT DOCUMENTS

| | | |
|---|---|---|
| 3,899,630 | 8/1975 | Puck . |
| 4,164,071 | 8/1979 | Kruzich . |
| 4,539,622 | 9/1985 | Akasaki . |
| 4,673,904 | 6/1987 | Landis . |
| 4,695,858 | 9/1987 | Takezawa et al. ............ 257/703 X |
| 4,909,909 | 3/1990 | Florjancic et al. . |
| 4,959,900 | 10/1990 | de Givry et al. . |
| 4,977,441 | 12/1990 | Ohtani et al. ................ 257/737 X |
| 5,261,826 | 11/1993 | Leeb . |
| 5,317,292 | 5/1994 | Leeb . |
| 5,319,330 | 6/1994 | Leeb . |

FOREIGN PATENT DOCUMENTS

| | | |
|---|---|---|
| 0146241 | 1/1987 | European Pat. Off. . |
| 0288767 | 11/1988 | European Pat. Off. . |
| 0312682 | 4/1989 | European Pat. Off. . |
| 0337331 | 10/1989 | European Pat. Off. . |
| 92-22995 | 12/1992 | European Pat. Off. ............. 29/846 |
| 455148 | 6/1988 | Sweden . |
| 2120861 | 12/1983 | United Kingdom . |

Primary Examiner—Carl J. Arbes
Attorney, Agent, or Firm—Burns, Doane, Swecker & Mathis

[57] ABSTRACT

In a method of manufacturing a circuit board having a lateral conductive pattern and shield regions, a first laminate of a substrate, covered on one side by a copper foil, is contour cut whereafter a second entirely covering copper foil is laminated to the second side of the substrate, and a conductive pattern of signal conductors and ground conductors is etched in the second copper foil. The second substrate is also contour cut and is laminated to a copper foil, whereafter a window is etched in the copper foil, corresponding to a window cut in the substrate. The second laminate thus formed is adjusted in regard of the pattern to the first laminate and is adhesively secured thereto, the side of the second laminate covered by the copper foil turned away from the wide of the first laminate provided with the conductive pattern. A metal layer is thereafter applied to the surface of the first laminate facing away from the side having the conductive pattern and the lateral edges to electrically connect the surface, the ground conductors of the conductive pattern and the foil on the second substrate, whereafter components are mounted in the windows in the second laminate to the conductive pattern.

17 Claims, 4 Drawing Sheets

METHOD OF MANUFACTURING CIRCUIT BOARD HAVING LATERAL CONDUCTIVE PATTERN

This application is a divisional of application Ser. No. 07/897,829, filed Jun. 12, 1992, now U.S. Pat. No. 5,298,684, issued Mar. 29, 1994.

RELATED APPLICATION

This application covers an aspect of an invention which is also covered by U.S. Pat. No. 5,317,292, entitled "A device with flexible, stripline conductors and a method of manufacturing such a device".

FIELD OF THE INVENTION

The present invention relates to a circuit board having a lateral conductive pattern and shielded regions as well as a method of manufacturing such a board.

BACKGROUND OF THE INVENTION

In electronic equipment for high frequencies and data signals having short transient times one portion in electronic equipment may interfere with the operation of other portions by the fact that the electromagnetical field will transfer signals over dielectric distances by induction. Such crosstalk will usually be dealt with by having the various portions of the equipment built into metal casings, which are electrically grounded and in the walls of which the electric field is short circuited, i.e. the casings will constitute shielded casings. The various portions are interconnected by coaxial cables. The signal being transferred on the coaxial cable may be purged from undesirable frequencies by means of special filters. The disadvantages of such shielded casings are partly that they are relatively costly, partly they are spaceconsuming. Another problem is that it is often difficult to provide sufficiently electromagnetically closed shields between the various portions of the electronic equipment in the case where one wants to integrate it on one single circuit board.

In conventional pattern boards often regions of the circuit board are surrounded by an etched and grounded frame incorporated in and surrounding the rest of the conductive pattern and further a ground plane is attached to the opposite side of the circuit pattern board. By soldering a metal shield on said grounded frame a region, which is fairly well but not completely shielded, is obtained. The problem in this case is that the electromagnetic radiation will leak laterally between the grounded frame and the ground plane in the laminate thus formed. This radiation can be partly confined by having holes drilled and metallized, which connect the ground plane and the grounded frame. The radiation leakage, however, may only be restricted in a certain amount in this way, since said holes cannot be located too closely to each other since this would impart a mechanical weakening of the laminate. Producing metallized holes in this way is, in addition, costly and constitutes a source of errors. Said method is particularly unsuitable for circuit boards intended for cheap and little space consuming surface mounting where holes are not required for the attachment of component legs but only as a connection between various conductive layers.

PRIOR ART

From the European patents 0 288 767 and 0 337 331 and the U.S. Pat. No. 4,673,904 it is previously known to prepare conductive patterns, where the conductors on all sides are enclosed by dielectrics and ground planes. The disadvantage of these prior methods is that a multitude of selective metal patterns and isolation patterns must be applied to a substrate in several sequential procedural steps what makes these methods complicated and the risk of having a bad manufacturing output is obvious. Another problem of this technique is that it is based on a deposition of metal on the substrate surface and that such deposited metal layers present a bad ductility. Further, this method is not compatible with what is generally established within the technique of manufacturing etched circuit pattern boards.

SUMMARY OF THE INVENTION

The purpose of the present invention is to provide a new and significantly simpler method for removing the disadvantages discussed above in the technique known up to this date, wherein conductive patterns are produced by etching a metal foil adhesively bonded to the substrate according to the established method of circuit pattern board manufacture and wherein in many cases rolled metal foil can be used which will produce a certain stretchability and flexibility in the manufactured card.

This purpose is achieved with a circuit board and a method of the kind indicated above having the characteristics set out in the appended claims.

Thus a circuit board having a lateral conductive pattern and shielded regions is provided comprising a first laminate of a substrate having a conductive pattern of signal conductors and ground conductors on one side and optionally an entirely covering copper foil on the other side, this first laminate being laminated with the side having a conductive pattern to another second laminate comprising a second substrate and a copper foil arranged on the side facing away from the first laminate, windows or apertures being cut in the substrate of the second laminate and etched away from its copper foil respectively in order to enable mounting of components to the conductive pattern inside the windows, and that a metal layer is arranged to electrically connect the optional, entirely covering foil of the first laminate with the ground conductors of the conductive pattern and the foil of the second laminate and also to cover the whole side of the first laminate where the optional entirely covering copper foil may be located, at least when such an optional copper foil is not arranged on this side.

According to advantageous embodiments of the circuit board of the invention the ground conductors of the conductive pattern are prepared with protruding portions such as contact tabs projecting past the edge of the substrate and the copper foil of the second laminate may likewise project past the second substrate edge in order to make a good contact with the metal layer connecting the ground planes of the board.

The method for the manufacture of the circuit boards thus comprises the following steps:

that a first isolating or dielectric substrate, which on one of the sides thereof may be coated with a conductive layer, such as a first copper foil, is cut, for instance by means of a laser beam or a water jet, to give the first substrate, together with the possible conductive layer, a desired outer contour or profile, whereafter another, first conductive layer, such as a first copper foil, is applied to, for instance laminated to, the other, first side of the first substrate to entirely cover said first side and the first conductive layer is etched to produce a conductive pattern comprising signal conductors and ground conductors on the first side of the first substrate and that a second isolating or dielectric substrate is cut to give it a desired outer contour or profile and windows or apertures through the thickness of said substrate and that it is coated with, for instance laminated to, a second conductive layer, such as a second copper foil, on one of its sides, the foil covering all of this first side, whereafter windows are etched in the second conductive layer corresponding to said windows or apertures cut in said second substrate, whereafter the second laminate formed in this way from the second substrate and the second conductive layer is placed on top of the first laminate in such a way that the second conductive layer of the second laminate is turned away from the first laminate and the first conductive layer having the conductive pattern of the first laminate is engaged with the other, second side of the second laminate and the two laminates are intimate attached to each other, for instance adhesively bonded to each other, and that a conductive layer such as a metal layer is applied to at least the marginal portions of that second side of the first laminate, which is turned away from the second laminate and thus may have a conductive layer, and the edges or marginal portions of the two laminates in order to electrically connect the said side of the first laminate, ground conductors of the conductive pattern on the first laminate and the third conductive layer on the second substrate, the application of this conductive metal layer being at least partly accomplished by means of thermal spraying of a low-melting metal, for instance tin or an alloy thereof, whereafter components are mounted in the windows or apertures in the second laminate to the circuit pattern of the first laminate.

According an advantageous embodiment of the invention metal caps are provided over the windows of one of the laminates, said metal caps being soldered or clamped firmly against the copper foil of the substrate in order to shield the window regions.

According to another advantageous embodiment of the invention portions of the optional copper foil of the side of the first laminate, which is opposite to the side having the conductive pattern, are etched away and masked against metal coating in order to enable access to the conductive pattern from this side.

SHORT DESCRIPTION OF THE FIGURES

Embodiments of the invention will now by way of example be described in more detail with reference to the accompanying drawings, in which FIG. 1 is a perspective view of two laminates comprised in the circuit board according to the invention, FIG. 2 is a cross sectional view of the finished circuit board, FIG. 3 is a cross sectional view of an alternative embodiment of the finished circuit board, FIG. 4 is a cross sectional view of the finished, mounted circuit board, FIG. 5 is a cross sectional view of a connecting portion along the lines V—V in FIG. 1, FIG. 6 is a cross sectional view illustrating ground connection in a component mounting region, FIG. 7 is a cross sectional view of an embodiment of a multilayer board and two laminates, FIGS. 8 to 13 illustrate different steps in the preparation of the two laminates, FIGS. 14 and 15 illustrate the assembly of the laminates and the final metallization step and FIGS. 16 and 17 illustrate alternative methods of attaching metal caps.

DESCRIPTION OF PREFERRED EMBODIMENTS

In the figures the thicknesses illustrated of the substrates and the foils are highly exaggerated in order to clarify the invention.

Figure 1:
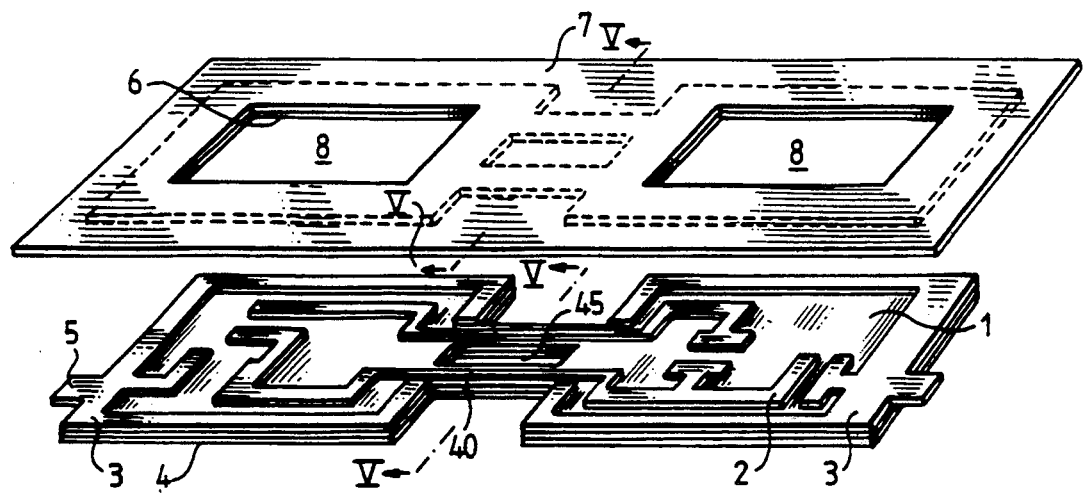

In FIG. 1 a dielectric first substrate 1 is shown which is contour cut by laser or a water jet and on which a conductive circuit pattern is located. The conductive pattern is etched from a conductive layer located on and attached to one side of the substrate 1, such as a copper foil adhesively bonded to said substrate, and it comprises conductors 2 for signals and ground conductors 3. The ground conductors 3, may as is shown in the figure, be located at the marginal portion of the substrate 1, in order to form a grounded frame surrounding the signal conductors 2. The conductive pattern 2, 3 may suitably be etched through a resist mask in the conventional way. From the ground conductors 3 contact tabs 5 project past the edge of substrate 1, these contact tabs being connected to or being part of the ground conductors 3.

Preferably another conductive metal layer such as a copper foil 4 is adhesively bonded to the other side of the substrate 1 and covers the entire surface of this other side.

A second laminate comprises a second substrate 6, which is cut by laser or a water jet and on which a metal layer such as a copper foil 7 is adhesively bonded or otherwise attached. The copper foil 7 extends past the edges of the substrate 6 to form a free copper marginal portion and portions of the copper foil 7 are etched away on locations corresponding to the windows 8 cut in the substrate 6 to form windows or apertures passing through the thickness of the second laminate.

Figure 2:
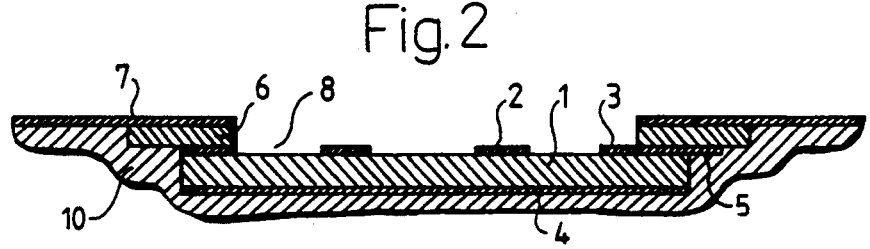

In FIG. 2 the two laminates of FIG. 1 are illustrated adhesively or otherwise bonded to each other in such a way that their patterns fit together, that is the circuit pattern 2, 3 of the first laminate is positioned correctly with respect to the windows 8 in the second laminate. They are arranged with the side of the substrate 1 having the circuit pattern brought into engagement with the surface of the second substrate 6 which is not coated with a metal foil. On the side, which is opposite to the windows 8, of the composite laminate illustrated in FIG. 2, a conductive layer is applied, preferably a layer 10 of tin or an alloy thereof, which is thermally sprayed such as by means of flame spraying and it will electrically connect the portions which are intended to be connected to a reference or ground potential, i.e. the entirely covering foil 4 on the other, second side of the first laminate, the tabs 5 extending from the grounded conductor frame 3 and the metal foil 7 bonded to the outer side of the second laminate. The bottom conductive layer 4 could in some cases be omitted but is generally preferred since it will ensure a could adhesion between the bottom of the completed circuit board and the thermally sprayed metal layer 10. Also, for an easy application the metal layer 10 covers all of the bottom surface of the composite board, but this is generally not required for the electrical shielding. The metal layer 5 may thus, as is illustrated in FIG. 3, cover only the edge regions of the completed board, also in order to perform the electrical connection mentioned above.

Figure 3:
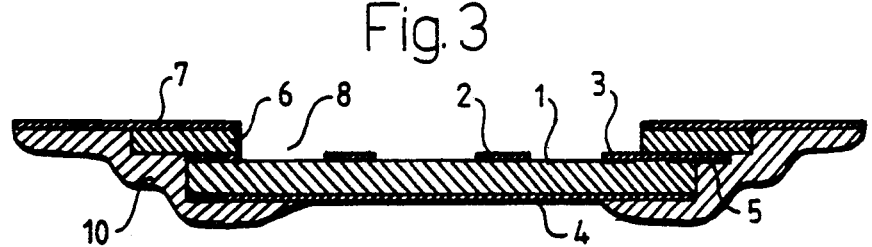

The two laminates illustrated in FIG. 1 are in the composite unit of FIGS. 2 and 3 fitted to each other in such a way that the inner edge of the windows 8 will enclose component mounting regions of the side having the conductive pattern of the substrate 1. At the locations where the second substrate 6 and the copper foil 7 of the second laminate cover the circuit pattern of the first laminate thus the circuit pattern will be enclosed between two ground planes 4, 7.

Figure 4:
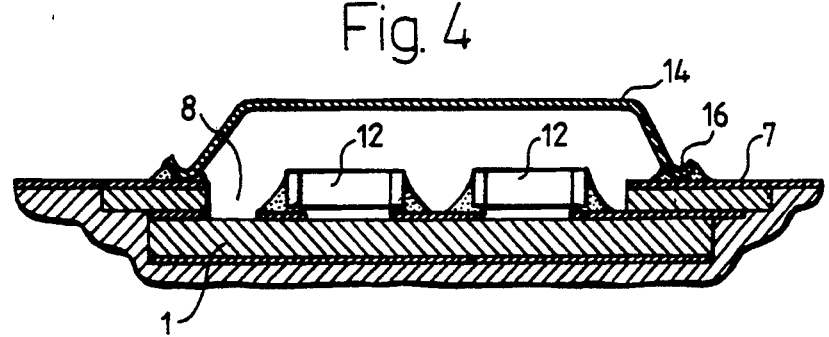

In the windows cut in the substrate 6 and in the copper foil of the second laminate electronic components 12 such as capacitors are intended to be mounted to the conductive pattern 2 on the inner side of the first laminate by means of surface mounting technique, see FIG. 4. After the component mounting these regions will be shielded by soldering a pressed metal cap, at 16, to the copper foil 7 on top of the second laminate, in such a way that the cap 14 will cover all of the window 8. Instead of soldering the cap 14 can be clamped or otherwise attached and electrically connected to the metal foil 7 covering the outer surface of the second laminate as will be further illustrated hereinafter.

Figure 5:
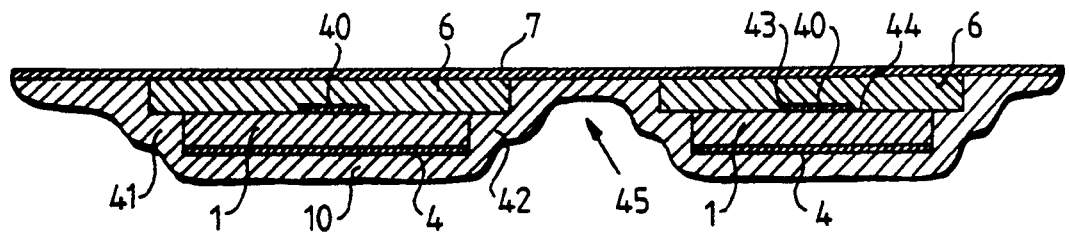

The regions for component mounting may be connected through portions, as is illustrated in FIG. 1 in the centrally located narrow portion, where elongated, band or strip shaped signal paths 40 of the signal conductors 2 are enclosed by the adhesively bonded substrates 1, 6 which constitute a dielectric, which in turn is enclosed by the ground planes 7, 4, which in turn are connected to each other by the tin layer 10, as has been mentioned above, compare FIG. 5. In this case the signal paths 40 may be surrounded at their longitudinal, lateral edges by portions 41, 42 of the tin layer 10. In order to accomplish this elongated windows 45 or apertures are arranged having their longitudinal edges at a suitable distance from the signal paths, at both of the edges of the signal paths 40 or at only one 43 of their edges, if the other edge 44 is located at the same suitable distance from the edge of the circuit board, these windows being made both in first laminate and in the substrate 6 of the second laminate, leaving the copper foil on the second substrate 6 to cover these windows. In this way the signal paths will be effectively shielded, also from each other with a constant impedance along their lengths between or in parallel with these windows 45. Inside the windows 45 the tin metal layer 10 will contact those left portions of the top copper foil 7. Also the edge profile of the finished circuit board may have the same steplike shape as illustrated for instance in FIG. 2, the edge of the second substrate 6 projecting past the edge of the first laminate inside the windows.

Figure 6:
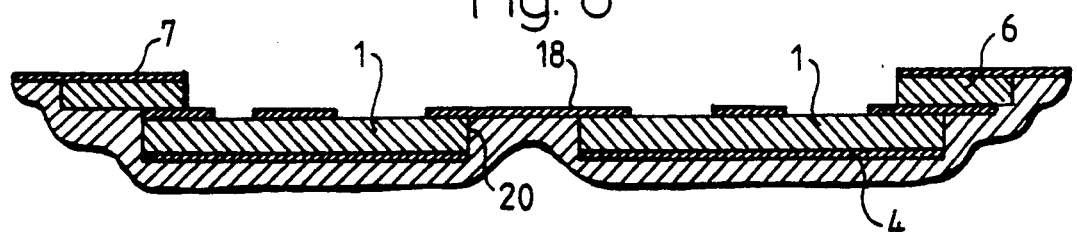

If an electrically grounded surface 18 is desired inside the grounded frame 3 and within the signal conductor pattern 2 a hole 20 is surface cut by means of laser or a water jet in the first substrate 1 of the first laminate, see FIG. 6, before the lamination of the first copper foil for the conductor pattern, and the corresponding parts of the bottom copper foil 4 on this first substrate are etched away. The copper foil, in which the conductive pattern is etched, will then cover the hole 20 and the thermally sprayed tin layer 10 will connect the ground planes 7, 18, and 4, as is illustrated in FIG. 6.

The method described above is suited for single conductive layers. If several conductive planes or intersections are required this is suitably accomplished by means of screen printing of isolating and conducting mixtures of artificial resins or plastics, so called polymer thick film technique. Suck a method for the manufacture of thin continuous substrate strips is described in the Swedish Patent 455 148, which is incorporated herein-as a reference.

Figure 7:
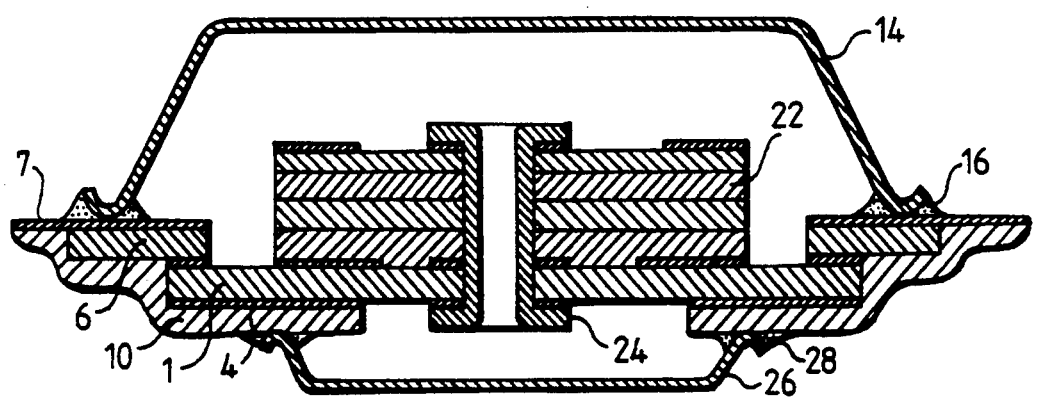

The copper foil 4 which may be arranged on the side opposite the side having the circuit pattern of the substrate 1 of the first laminate can be etched and masked against metallization in order to provide access to the circuit also from this side. Such regions may then be shielded by electrically closed metal caps 26, as is illustrated in FIG. 7, wherein an embodiment is illustrated consisting of two laminates, combined with a multilayer board 22 located on top of the above mentioned conductive pattern comprising the signal and ground conductors 2, 3. The contacting of the conductive planes incorporated in the multilayer board and the conductors 2, which have been etched on the substrate 1, is accomplished by means of metallized holes 24. In this case the metal layer 10 on the bottom and edges of the circuit board and the metal layer inside and at top and bottom of the through-holes may advantageously be prepared at the same time by metal plating, as is conventionally used in metallization of through-holes in multilayer circuit pattern boards.

The multilayer board 22 is prepared according to conventional circuit board technique and the other laminates are prepared as has been described above. The laminates are drilled and the holes are coated according to prior multilayer board methods wherein the regions of the ground plane 4 of the lower laminate of FIG. 7, where the coated hole 24 will be produced, is etched away and the hole 24 is connected to the signal conductors of the multilayer board 20. The ground planes 4, 7 are contacted through a simultaneously deposited metal layer 10, as has already been mentioned. In this embodiment shield caps 14, 26 are mounted at the ground planes 7, 10 by means of soldering joints 16 and 28 respectively in order to shield the circuit space completely.

Circuit boards can thus be laminated with composite devices as has been described above and the conductors thereof are electrically connected by drilled and metal coated holes in regions, where the copper foil have been etched away and the metallization has been masked.

An example of the method according to the invention for the preparation of circuit boards having a lateral conductive pattern and shielded regions of the kind illustrated in FIG. 2 will now be described in more detail with reference to FIGS. 8 -15.

Figure 8:
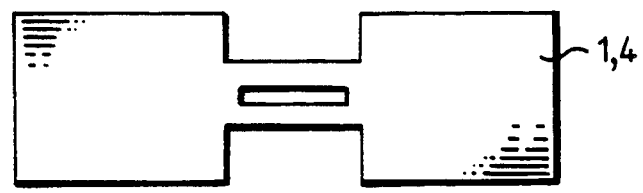

A laminate of a substrate 1 of 0.2 mm thick glass fibre reinforced plastics is coated with 0.035 mm thick copper foil 4 on one side and is contour cut by means of laser, see FIG. 8.

A laminate cut in this way is laminated in a hydraulic press provided with a suitable heating to a larger copper foil 11, similarly having a thickness 0.035 mm. The same adhesive is used as a bonding agent, see FIG. 9.

The substrate coated on both sides is then coated by dipping in a photo resist. A pattern is exposed and is etched in the copper foil 11, this pattern constituting signal conductors 2 and ground planes 3. At suitable places contact tabs or contact tongues 5 project past the edge of the substrate 1, see FIG. 10.

Figure 9:
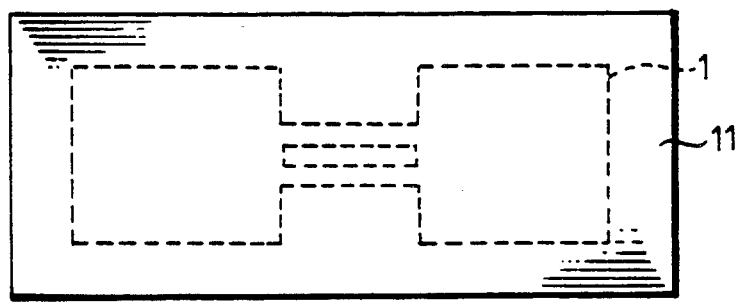
Figure 10:
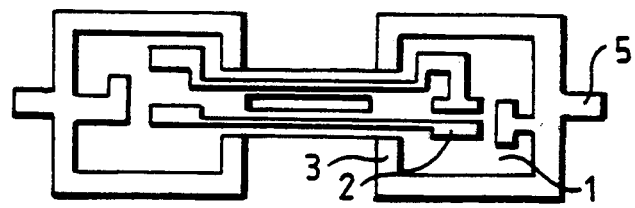
Figure 11:
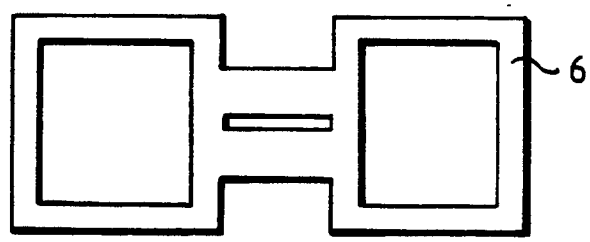
Figure 12:
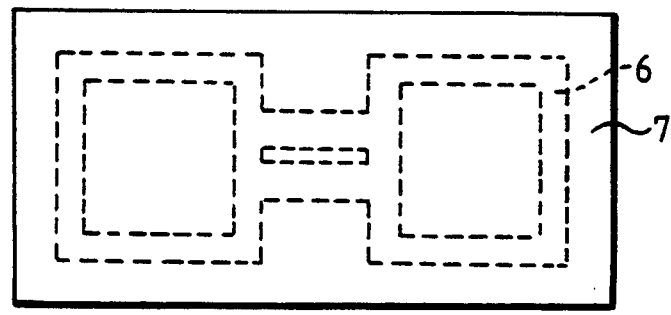
Figure 14:
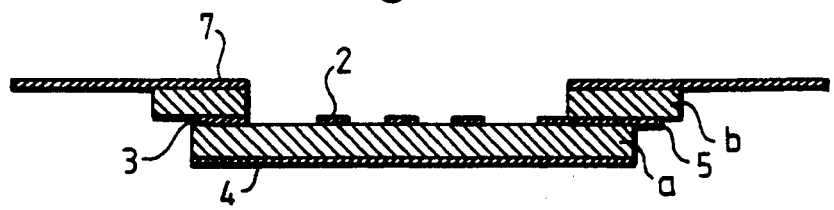

The laminate a prepared in this way according to FIGS. 8-10 constitutes a first intermediate product, compare FIG. 14.

The second substrate 6, similarly consisting of 0.2 mm thick glass fibre reinforced plastics but not coated with a copper foil on any of its sides is contour cut by means of laser. The substrate 6 cut in this way is 0.5 to 1 mm larger than the first intermediate product a, this dimension being chosen to have the same order of magnitude as the thicknesses of the laminates in order to make the marginal portions of the sprayed metal layer 10 extend not perpendicularly to the surfaces of the laminates and at a small angle of about 5 to 45 degrees, see FIG. 11.

The cut substrate 6 is laminated to a larger copper foil 7, which thus will project past the edges of the substrate 6. The thickness of the copper foil is as before 0.035 mm. The projecting portion of the copper foil 7 may then also have a width of the same magnitude of order as the thickness of the laminates, see FIG. 12.

Figure 13:
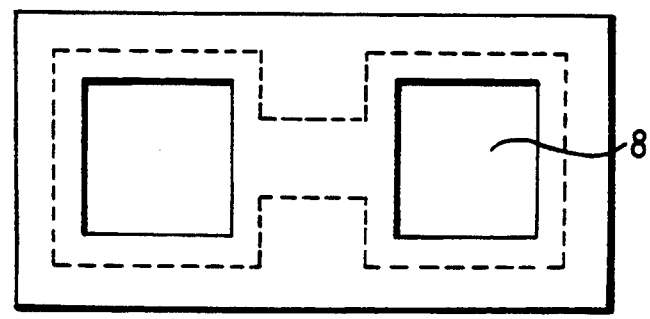

The laminate 6, 7 formed in this way is coated with a photo resist by dipping and is exposed and etched in order to form windows 8, see FIG. 13.

The laminate prepared in this way constitutes a second intermediate product b, compare FIG. 14.

The first and second intermediate products a, b are adhesively bonded to each other in such a way that their contours coincide in the desired way, see FIG. 14. The bonding is accomplished in a heated hydraulic press.

Figure 15:
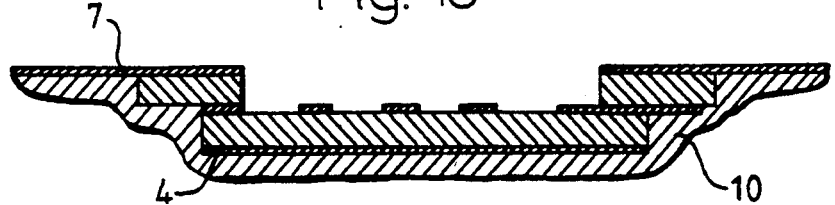

The bonded product is flame sprayed with tin 10 on the side opposite to the side having the windows 8 and the conductive pattern, see FIG. 15, whereby the ground planes 4, 5 and 7 are electrically connected. In this operation the contact tabs 5 of the grounded frame 3 and the portion of the foil 7 projecting past the substrate edge function to ensure a good electrical contact with the metal layer 10. Before spraying of the metal layer 10 it is important that the copper foil and the contact tabs should have been cleaned from remaining adhesive.

Figure 16:
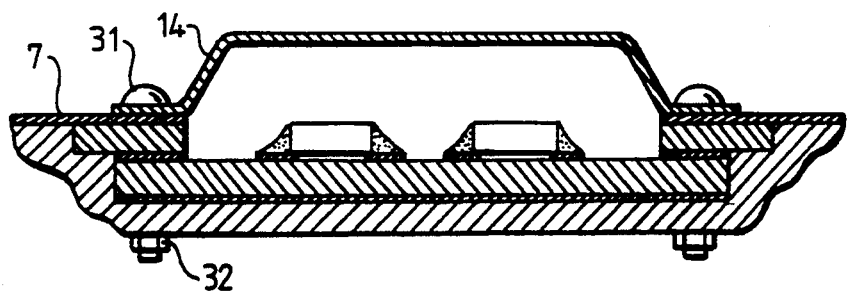
Figure 17:
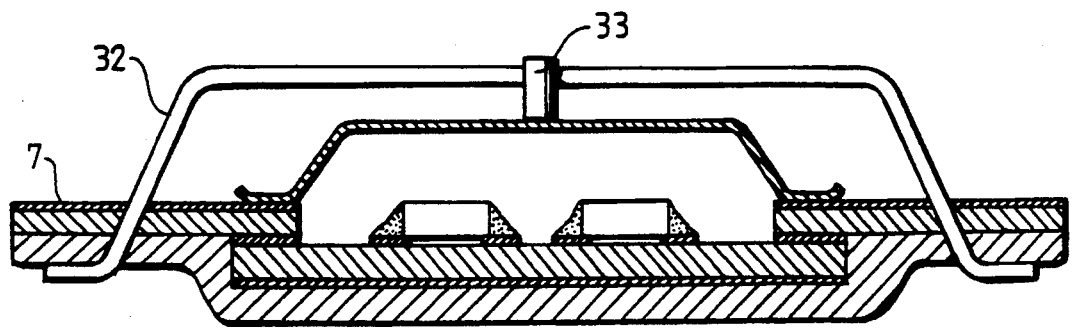

In FIGS. 16 and 17 two alternative methods of attaching the metal caps 14 over the component mounting areas are illustrated, which methods could also be used for the metal caps on the bottom side of the finished circuit board. Thus in the construction illustrated in FIG. 16 bolts 31 are inserted through holes in the metals caps 14 and the thickness of the circuit board and the force from nuts 32 tightened on the bolts 31 presses the metal cap 14 onto the top copper foil 7. In the alternative illustrated in FIG. 17 the metal cap 14 is pressed to contact the copper foil 7 along the periphery thereof by a bent metal wire 32 which is inserted through holes in the thickness of the circuit board. An intermediate element 33 such as a wedge shaped means may be used between the bent element 32 and the top portion of the metal cap 14 to ensure a correct pressing force.

The invention can be modified by anyone skilled in the art. Thus for instance instead of localized contact tabs 5 projecting from the outer margin of the conductive pattern the tabs can be continuous and extend all the way along some or all of the edges of the first substrate 1. Also, the projecting margin of the conductive layer 7 on top of the second substrate 6 may not be continuous and comprise tab portions, but this would reduce the adhesive force of the metal layer 10.

I claim:

1. A method for the manufacture of circuit boards having a lateral conductive pattern and shielded regions, comprising the steps
    providing a first laminate comprising
        a first isolating or dielectric substrate, and
        a first conductive layer comprising a conductor pattern including signal conductors and ground conductors located on a first side of the first substrate;
    providing a second laminate comprising
        a second isolating or dielectric substrate, and
        a second conductive layer located on a first side of the second substrate;
    making windows through the thickness of the second laminate,
    placing the second laminate on top of the first laminate such that the second conductive layer of the second laminate is turned away from the first laminate and the first conductive layer thereon having the conductive pattern are engaged with a second side of the second laminate and the two laminates are attached to each other; and
    arranging a third conductive layer on a second side of the first laminate, which is turned away from the second laminate, and edges or marginal portions of the two laminates to electrically connect the ground conductors of the conductive pattern on the first laminate and the second conductive layer on the second substrate.

2. A method as claimed in claim 1, wherein
    in providing the first laminate
    the first isolating or dielectric substrate is given a desired outer contour or profile,
    whereafter the first conductive layer is produced on the first side of the first substrate,
    in providing the second laminate and making the windows
    the second isolating of dielectric substrate is given a desired outer contour or profile
    whereafter windows are produced through the thickness of the second substrate,
    whereafter the second conductive layer is produced on the first side of the second substrate,
    whereafter windows or apertures are produced in the second conductive layer corresponding to said windows in said second substrate.

3. A method as claimed in claim 2, wherein a side of the first substrate is coated with a fourth conductive layer before it is given the desired contour or profile.

4. A method is claimed in claim 3, wherein in arranging the third conductive layer a fifth conductive layer is applied at least to marginal portions of a second side of the first laminate, which is turned away from the second laminate and has the fourth conductive layer.

5. A method as claimed in claim 3, wherein portions of the fourth conductive layer on the side opposite the side having the conductive pattern of the first laminate are etched away, said portions of said fourth conductive layer thus not being covered by any conductive coating in order to enable access to the conductive pattern through the first substrate.

6. A method as claimed in claim 2, wherein the first conductive layer is etched to produce the conductive pattern including the signal conductors and ground conductors.

7. A method as claimed in claim 2, wherein the windows or apertures are etched in the second conductive layer.

8. A method as claimed in claim 1, wherein the placing the second laminate on top of the first laminate the two laminates are adhesively bonded to each other.

9. A method as claimed in claim 1, wherein on top of said windows in the second laminate metal caps are attached to the second conductive layer of the second substrate.

10. A method as claimed in claim 1, wherein said third conductive layer is at least partly applied by means of thermal spraying of a low-melting metal.

11. A method as claimed in claim 1, wherein windows are also made in the first substrate where these windows are protected from obtaining any conductive layer on the other, second side of the first laminate, in order to enable access to the conductive pattern through the first laminate.

12. A method as claimed in claim 11, wherein portions, corresponding to said windows in the first substrate, of a fourth conductive layer on the side opposite to the side having the conductive pattern of the first laminate are etched way and masked against any conductive coating.

13. A method as claimed in claim 1, wherein circuit pattern boards are laminated to the first laminate and holes are drilled and coated with a conductive layer to connect conductors of the other circuit pattern boards to the circuit pattern of the first laminate.

14. A method as claimed in claim 9, wherein the metal caps are soldered to the second conductive layer of the second substrate.

15. A method as claimed in claim 9, wherein the metal caps are clamped to the second conductive layer of the second substrate.

16. A method as claimed in claim 10, wherein the low-melting metal is tin.

17. A method as claimed in claim 10, wherein the low-melting metal is tin alloy.

* * * * *